US011666719B2

(12) United States Patent
Gerder

(10) Patent No.: US 11,666,719 B2
(45) Date of Patent: Jun. 6, 2023

(54) CONTROL SYSTEM AND PROCESS FOR CONTROLLING A BREATHING GAS CIRCUIT IN A CLOSED-CIRCUIT RESPIRATOR

(71) Applicant: Dräger Safety AG & Co. KGaA, Lübeck (DE)

(72) Inventor: Henning Gerder, Lübeck (DE)

(73) Assignee: Dräger Safety AG & Co. KGaA, Lübeck (DE)

(*) Notice: Subject to any disclaimer, the term of this patent is extended or adjusted under 35 U.S.C. 154(b) by 603 days.

(21) Appl. No.: 16/717,032

(22) Filed: Dec. 17, 2019

(65) Prior Publication Data

US 2020/0188618 A1 Jun. 18, 2020

(30) Foreign Application Priority Data

Dec. 18, 2018 (DE) .................. 10 2018 009 804.5

(51) Int. Cl.
*A61M 16/00* (2006.01)
*A61M 16/10* (2006.01)
(Continued)

(52) U.S. Cl.
CPC ...... *A61M 16/024* (2017.08); *A61M 16/0003* (2014.02); *A61M 16/0891* (2014.02);
(Continued)

(58) Field of Classification Search
CPC .......... A61M 16/0003; A61M 16/0891; A61M 16/1075; A61M 16/22; A61M 16/024;
(Continued)

(56) References Cited

U.S. PATENT DOCUMENTS 4,635,629 A * 1/1987 Thorp .................. B63C 11/24
128/205.12
5,269,293 A * 12/1993 Loser .................. F25B 17/08
128/204.15
(Continued)

FOREIGN PATENT DOCUMENTS

DE 29814738 U1 4/1999
DE 102007048597 A1 4/2009
(Continued)

*Primary Examiner* — Michael J Tsai
(74) *Attorney, Agent, or Firm* — McGlew and Tuttle, P.C.

(57) ABSTRACT

A control system, for controlling a closed-circuit respirator breathing gas circuit, includes a temperature sensor, a temperature-reading unit and with a control unit. The temperature sensor is configured to send a temperature signal in the presence of a corresponding temperature polling. The temperature signal indicates the temperature currently present in an area surrounding the temperature sensor. The temperature-reading unit is arranged in the closed-circuit respirator at a spaced location from the breathing gas circuit and the temperature sensor, and is configured to trigger the temperature polling at the temperature sensor by sending a polling signal, and to receive the temperature signal sent by the temperature sensor. The control unit is signal connected to the temperature-reading unit and is configured to determine the temperature indicated by the temperature signal in the area surrounding the temperature sensor and to output a control signal as a function of this temperature.

20 Claims, 5 Drawing Sheets

(51) Int. Cl.
*A61M 16/22* (2006.01)
*A61M 16/08* (2006.01)

(52) U.S. Cl.
CPC ........ *A61M 16/1075* (2013.01); *A61M 16/22* (2013.01); *A61M 2205/3606* (2013.01); *A61M 2230/50* (2013.01)

(58) Field of Classification Search
CPC ...... A61M 2205/3606; A61M 2230/50; A62B 9/003; A62B 7/00
See application file for complete search history.

(56) References Cited

U.S. PATENT DOCUMENTS

| | | | |
|---|---|---|---|
| 6,563,417 | B1 | 5/2003 | Shaw |
| 6,847,912 | B2 | 1/2005 | Forster |
| 6,953,919 | B2 | 10/2005 | Clothier |
| 2011/0088693 | A1* | 4/2011 | Somervell ......... A61M 16/1095 |
| | | | 128/203.14 |
| 2015/0007820 | A1* | 1/2015 | Koch .................... A62B 19/00 |
| | | | 128/204.15 |
| 2015/0377544 | A1* | 12/2015 | Nelson ................. G01K 1/024 |
| | | | 374/117 |
| 2016/0213879 | A1 | 1/2016 | Chuang et al. |
| 2016/0199673 | A1* | 7/2016 | Berkson ................ A62B 9/003 |
| | | | 128/202.26 |
| 2016/0250504 | A1* | 9/2016 | Koch ...................... A62B 7/02 |
| | | | 128/204.15 |
| 2017/0021202 | A1* | 1/2017 | Koch .................... A62B 9/006 |
| 2019/0184212 | A1 | 1/2019 | Frazzoli et al. |

FOREIGN PATENT DOCUMENTS

| | | | |
|---|---|---|---|
| DE | 102008055700 A1 | 5/2010 | |
| DE | 102013016601 B4 | 9/2015 | |
| GB | 2464802 A | * 5/2010 | ........ A61M 16/1075 |

* cited by examiner

CONTROL SYSTEM AND PROCESS FOR CONTROLLING A BREATHING GAS CIRCUIT IN A CLOSED-CIRCUIT RESPIRATOR

CROSS REFERENCE TO RELATED APPLICATIONS

This application claims the benefit of priority under 35 U.S.C. § 119 of German Application 10 2018 009 804.5, filed Dec. 18, 2018, the entire contents of which are incorporated herein by reference.

TECHNICAL FIELD

The present invention pertains to a control system for controlling a breathing gas circuit in a closed-circuit respirator, to a closed-circuit respirator and to a process for controlling a breathing gas circuit in a closed-circuit respirator.

TECHNICAL BACKGROUND

The use of a cooling device in a closed-circuit respirator for cooling a breathing gas stream is known and necessary. Thus, a lime material (soda lime), which is typically used as an absorber for treating the gas and which treats the breathing gas by removing $CO_2$, produces heat continuously. In the closed breathing circuit, this causes, over the duration of use of the closed-circuit respirator, the temperature of the inhaled gas to rise for the user of the closed-circuit respirator into a temperature range that is at least extremely uncomfortable for the user during the inhalation. Provisions are therefore made for a continuous cooling of the breathing gas circuit by a cooling device. The cooling device has a coolant, which is typically cooled to below its melting point prior to the use of the closed-circuit respirator.

The coolant is preferably ice or a coolant, which is configured as a phase-change material (PCM) and is used within a liquid container/heat exchanger in the closed-circuit respirator.

In preparation for a use of the closed-circuit respirator, a quantity of oxygen carried along in a pressurized gas cylinder of the closed-circuit respirator, a dimensioning of a quantity of lime carried along for a $CO_2$ absorber and a quantity of coolant in the cooling device are typically adapted to one another. Such an adaptation is carried out by taking into consideration necessary safety reserves along with an also desirable optimization of the weight.

SUMMARY

An object of the present invention is to provide an improved control for a closed-circuit respirator, especially an improved control of the cooling device in a closed-circuit respirator.

To accomplish the object, a control system is provided according to the present invention for controlling a breathing gas circuit in a closed-circuit respirator, with a temperature sensor, with a temperature-reading unit and with a control unit.

The temperature sensor, especially the temperature sensor unit embodied by means of a radio frequency identification (RFID) tag including a temperature sensor, is configured to send a temperature signal in the presence of a corresponding temperature polling, the temperature signal indicating the temperature currently present in a surrounding area. The temperature sensor is arranged in this case in (connected to/as a part of) the closed-circuit respirator such that the temperature present in the area surrounding the temperature sensor indicates a breathing gas temperature in an area of the breathing gas circuit in the closed-circuit respirator.

The temperature-reading unit, especially the temperature-reading unit embodied as an RFID reading unit, is arranged in the closed-circuit respirator at a spaced location from the breathing gas circuit and from the temperature sensor unit and is signal connected preferably in a wireless manner to the temperature sensor. It is configured to trigger the temperature polling at the temperature sensor by sending a polling signal, and it is further configured to receive the temperature signal sent by the temperature sensor.

The control unit is arranged in the closed-circuit respirator at a spaced location from the breathing gas circuit and from the temperature sensor and is connected for signal technology to the temperature-reading unit. The control unit is configured, furthermore, to determine the temperature in the area surrounding the temperature sensor, which temperature is indicated by the temperature signal, and to output a control signal depending on this temperature. The control signal is preferably suitable for triggering a control output at a user interface of the closed-circuit respirator.

The present invention is based on the discovery that the usability of the cooling device of the closed-circuit respirator, especially the remaining duration of use thereof, can be estimated especially well by a control of the temperature of the inhaled gas during a use. The temperature sensor, whose measurement is received and analyzed by units located at spaced locations, is provided according to the present invention for this control.

The solution according to the present invention makes it advantageously possible to determine a temperature within the breathing gas circuit during the use of the closed-circuit respirator. In addition to the known control of the consumed quantity of oxygen in the pressurized gas cylinder, an additional important parameter of the closed-circuit respirator can be monitored hereby. In particular, the temperature sensor makes it advantageously possible to forecast a future development of the temperature of the inhaled gas, as a result of which it becomes advantageously possible to plan a future duration of use. In addition, a current temperature of the inhaled gas can be determined, for example, in order to ensure that a temperature limit value of about 42° C. will not be exceeded. The control system can therefore advantageously improve the safety of the use of a correspondingly configured closed-circuit respirator.

Another advantage of the control system according to the present invention is the separation in space between the temperature sensor and the temperature-reading unit. It is possible as a result that the temperature-reading unit and the control unit are arranged within a central control system of the closed-circuit respirator. Furthermore, it is made possible by the separation in space that the temperature sensor can be arranged at an especially suitable location in the areas of the breathing gas circuit.

The simple integration of the control system according to the present invention in existing closed-circuit respirators is also advantageous. Thus, only known structural shapes of the temperature sensor and of the temperature-reading unit need to be installed in existing closed-circuit respirators in a suitable manner. In particular, the control unit may be integrated in an existing central control system.

The sending of the temperature signal may be affected by a modulation of an electromagnetic field provided by the temperature-reading unit, as it is known, for example, for a communication by means of RFID technology. The temperature-reading unit is configured in this case to detect such modulation and to receive the signal as a result.

Preferred embodiments of the control system according to the present invention will be described below.

In a preferred embodiment, the control signal outputted by the control unit is suitable for triggering a control output at a user interface of the breathing gas circuit system. The user interface may be configured to output an optical or acoustic warning if the determined temperature is above a predefined temperature limit value. In one variant of this embodiment, the user interface is arranged at the closed-circuit respirator. In an alternative variant, the user interface is a mobile, external device, which receives the control signal by a transmission unit arranged in the closed-circuit respirator.

In an especially preferred embodiment, the temperature sensor unit comprises a passive RFID tag incorporating a temperature sensor. The transmission of the temperature signal is typically carried out for a passive RFID tag such that an electromagnetic field generated by the temperature-reading unit supplies the passive RFID tag with energy and is modulated by the RFID tag in a temperature-dependent manner. The configuration of an RFID tag suitable for the temperature measurement is known and will not therefore be explained in detail below. Reference shall be made here to the documents U.S. Pat. Nos. 6,563,417 B1, 6,847,912 B2 and 6,953,919 B2 (6,563,417 B1, 6,847,912 B2 and 6,953,919 B2 are each are incorporated herein by reference) as examples describing the function and typical RFID technology that is used.

An advantage of this embodiment is the elimination of the need for an energy supply unit connected to the temperature sensor. As a result, a permanent arrangement of the RFID tag in the area of the breathing gas circuit is made possible, because it is not necessary, for example, to change batteries at the temperature sensor. The low manufacturing cost and the simple use of existing related technologies are also advantageous in case of the use of an RFID tag in general. In an alternative embodiment, the temperature sensor unit has an energy supply unit, especially an energy supply unit embodied by means of batteries. In a preferred variant of this alternative embodiment, the temperature sensor unit is an active RFID tag. The active RFID tag is preferably configured to actively send the temperature signal to the temperature-reading unit. The control system according to the alternative embodiment makers possible a comparatively great distance between the temperature sensor and the temperature-reading unit compared to the theoretically possible distance in case of the use of a passive RFID tag, which is typically in the range of a few decimeters. The transmission of the temperature signal is carried out by means of an active RFID tag such that a temperature-measuring device is operated by means of a battery or of a rechargeable battery, which is charged by an electromagnetic field provided by the temperature-reading unit. The temperature signal determined by the temperature-measuring device is then sent to the temperature-reading unit either by a modulation of the electromagnetic field provided or by a wireless transmission.

In another embodiment, the temperature sensor unit is connected to the temperature-reading unit in a wireless manner. As a result, cables are eliminated within the closed-circuit respirator, which reduces the fault liability of the control system due, for example, to cable break. Furthermore, the weight of the closed-circuit respirator is reduced hereby.

In another preferred embodiment, the temperature sensor unit is arranged in the breathing gas circuit of the closed-circuit respirator. As a result, the temperature within the breathing gas circuit can advantageously be determined directly. The control system according to this embodiment has an especially low fault liability compared to a control system in which the temperature sensor is arranged outside the breathing gas circuit. The temperature sensor unit is preferably arranged in this embodiment in an area of the breathing gas circuit in which contamination of or damage to the temperature sensor is unlikely.

In an especially preferred variant of the previous embodiment, the temperature sensor unit is arranged in the cooling device of the closed-circuit respirator or in a supply line between the cooling device and the user of the closed-circuit respirator. The determination of the temperature within the supply line makes it advantageously possible to determine the temperature the inhaled gas has directly at the user of the closed-circuit respirator. This makes it possible to infer whether the cooling effect of the cooling device is sufficient for the further use of the closed-circuit respirator. This makes it furthermore possible to infer how long the cooling effect of the cooling device will still be sufficient for the further use of the closed-circuit respirator. The cooling device is preferably provided for cooling the breathing gas circuit directly before an output of the inhaled gas to the user. The arrangement of the temperature sensor unit in the cooling device makes it therefore likewise possible to determine the temperature of the inhaled gas that is directly being inhaled by the user. In a variant of this embodiment, the temperature sensor is arranged in the cooling device such that the determined temperature is the temperature present directly at a coolant of the cooling device. As a result, it is possible in an especially advantageous manner to infer a cooling effect of the cooling device that is currently present during the use.

In another embodiment, the control unit is configured to determine a coolant state of the cooling device on the basis of the determined temperature, wherein the coolant state indicates an expected further cooling time of the cooling device, and to output the control signal on the basis of the coolant state. A piece of directly usable information concerning the further cooling time is especially advantageously outputted in this embodiment. A possibly difficult interpretation of a mere temperature value is circumvented thereby. In particular, an analysis of the control signal by a user of the closed-circuit respirator is made possible. The user maybe, in this case, the carrier of the closed-circuit respirator during the use, or the user may be another person, who monitors the use in terms of use data or retrospectively analyzes a use.

In an especially preferred embodiment, the control system has at least one comparison temperature sensor unit, especially a comparison temperature sensor unit embodied as an RFID tag including a temperature sensor, which is configured to send a comparison temperature signal in the presence of a corresponding comparison temperature polling, wherein the comparison temperature signal indicates the comparison temperature currently present in the area surrounding the at least one comparison temperature sensor unit. The temperature-reading unit is further configured to trigger the comparison temperature polling at the at least one comparison temperature sensor unit by sending a comparison temperature signal, and it is further configured to receive the comparison temperature signal sent by the comparison temperature sensor. The control unit according to the present invention is correspondingly configured, furthermore, to determine the comparison temperature indicated by the comparison temperature signal and to output the control signal depending on the temperature and the comparison temperature. The determination of the comparison temperature makes it advantageously possible to better analyze the temperature determined by the temperature sensor, for example, against the background of an expected further cooling time of the cooling device, which is to be determined. Furthermore, the determination of the comparison temperature makes it additionally possible to control the temperature of an additional area of the closed-circuit respirator.

The control unit is configured in an especially preferred variant of the previous embodiment to output the control signal depending on a temperature difference between the comparison temperature and the temperature. An effectively occurring cooling can especially advantageously be determined thereby, for example, by a comparison of the outside temperature or another comparison and the cooled inhaled gas. As a result, errors in the assessment of the residual cooling time, which develop due to the fact that, for example, the outside temperature is higher than expected, can be avoided. The utilization of a temperature difference makes it consequently possible to estimate an expected further cooling time of the cooling device in an especially reliable manner.

In an additional, preferably supplementary variant of the above embodiment, the at least one comparison temperature sensor is arranged in a supply line between the cooling device and the user of the closed-circuit respirator, in a breathing bag of the closed-circuit respirator at a housing of the closed-circuit respirator or at a $CO_2$ absorber unit of the closed-circuit respirator. In the case in which the comparison temperature sensor is arranged in the supply line, the temperature sensor is not preferably arranged in the supply line. The arrangement in the breathing bag makes it advantageously possible to compare a breathing gas temperature at the beginning of the breathing gas circuit to a temperature of the inhaled gas in the vicinity of an outlet of the breathing gas circuit. An arrangement of the comparison sensor at the housing of the closed-circuit respirator makes it advantageously possible to make a comparison between an ambient temperature of the closed-circuit respirator and the temperature of the inhaled gas at the user. In an example of this variant, the comparison temperature sensor is arranged at an outer surface of the housing of the closed-circuit respirator. As a result, an ambient temperature can be measured directly. In an alternative example, the comparison temperature sensor is arranged at an inner surface of the housing. As a result, a general operating temperature within the closed-circuit respirator can be determined. The arrangement of the comparison temperature sensor at the $CO_2$ absorber unit makes it advantageously possible to directly determine the temperature difference by which the breathing gas was cooled down by the cooling device.

In an especially preferred embodiment, the temperature sensor unit is configured, furthermore, to provide the temperature signal such that it contains identification information of the temperature sensor, the identification information permitting unambiguous assignment between the temperature sensor unit and the temperature signal. The identification information makes it advantageously possible for the control unit to ensure that the determined temperature originates from the sensor arranged in the closed-circuit respirator. In an especially advantageous variant of this embodiment, the control system comprises a plurality of temperature sensor units. The identification information makes possible in this case an unambiguous assignment between the temperature signal and a respective temperature sensor unit from the plurality of temperature sensor units.

In another advantageous variant of the previous embodiment, the control system has the temperature sensor unit and the comparison temperature sensor unit. As a result, a single polling signal can advantageously be sent to the temperature sensor unit and to the comparison temperature sensor unit. The comparison polling signal and the polling signal are consequently the same signal. Furthermore, the temperature-reading unit receives the temperature signal and the comparison temperature signal via a single antenna array, and a differentiation is made between the comparison temperature signal and the temperature signal by the respective included identification information.

In another embodiment, the control system according to the present invention comprises at least one additional temperature sensor unit and/or comparison temperature sensor unit. As a result, an improved and especially more detailed control of the temperature can be made possible within the closed-circuit respirator.

To accomplish the object according to the present invention, a closed-circuit respirator is, furthermore, provided, which comprises a control system in accordance with at least one of the above embodiments. The closed-circuit respirator according to the present invention consequently has all the advantages of the control system according to the present invention.

According to another aspect of the present invention, a process for controlling a breathing gas circuit in a closed-circuit respirator, which process has the following steps, is provided including:

provision of a temperature sensor, especially of a temperature sensor embodied by means of an RFID tag, such that a temperature present in an area surrounding the temperature sensor indicates a breathing gas temperature in an area of the breathing gas circuit in the closed-circuit respirator;

arrangement of a temperature-reading unit, especially of a temperature-reading unit embodied by means of an RFID tag, at a spaced location from the breathing gas circuit and from the temperature sensor;

provision of a control unit at a spaced location from the breathing gas circuit and from the temperature sensor and connection of the control unit for signal technology to the temperature-reading unit;

sending of a polling signal to trigger a temperature polling by the temperature-reading unit at the temperature sensor;

sending of a temperature signal in the presence of the corresponding temperature polling by the temperature sensor, wherein the temperature signal indicates the temperature currently present in an area surrounding the temperature sensor;

reception of the temperature signal sent by the temperature sensor; and determination of the temperature indicated by the temperature signal in the area surrounding the temperature sensor, and outputting of a control signal as a function of this temperature.

The process according to the present invention according to the additional aspect of the present invention is carried out by the control system according to the present invention. The process consequently has all the advantages of the control system according to the present invention.

In an especially preferred embodiment of the process according to the present invention, the outputting of the control signal by the control unit comprises the following steps:
- determination of a coolant state of a cooling device of the closed-circuit respirator on the basis of the temperature determined, wherein the coolant state indicates an expected cooling time of the cooling device; and
- outputting of the control signal on the basis of the coolant state.

The control signal according to this embodiment can be used in an especially simple manner for a further processing, for example, for a control output at a user interface of the closed-circuit respirator. Furthermore, the determination of the expected further cooling time makes it advantageously possible to improve the planning of the further use of the closed-circuit respirator.

In another embodiment, the process according to the present invention comprises, furthermore, the steps of
- providing at least one comparison temperature sensor, especially a comparison temperature sensor embodied by means of an RFID tag, in the closed-circuit respirator;
- sending a comparison polling signal by the temperature-reading unit to trigger a comparison temperature polling at the at least one comparison temperature sensor;
- sending a comparison temperature signal in the presence of the corresponding comparison temperature polling, wherein the comparison temperature signal indicates the comparison temperature currently present in an area surrounding the at least one comparison temperature sensor;
- receiving the comparison temperature signal sent by the comparison temperature sensor; and
- determining the comparison temperature indicated by the comparison temperature signal, and outputting the control signal as a function of the temperature and the comparison temperature.

The provision of a comparison temperature makes it possible to improve the analysis of the temperature determined by the temperature sensor. In an especially preferred variant of this embodiment, the control signal is outputted as a function of a temperature difference between the comparison temperature and the temperature. The determination of a temperature difference according to this variant makes it possible in an especially advantageous manner to determine the actual existence of cooling by the cooling device of the closed-circuit respirator. In particular, a difference between a heated $CO_2$ absorber and cooled inhaled gas and/or a difference between an outside temperature and cooled inhaled gas can be determined and used as the basis for the control signal to be outputted.

The present invention shall be explained now in more detail on the basis of advantageous exemplary embodiments shown schematically in the figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF PREFERRED EMBODIMENTS

Figure 1:
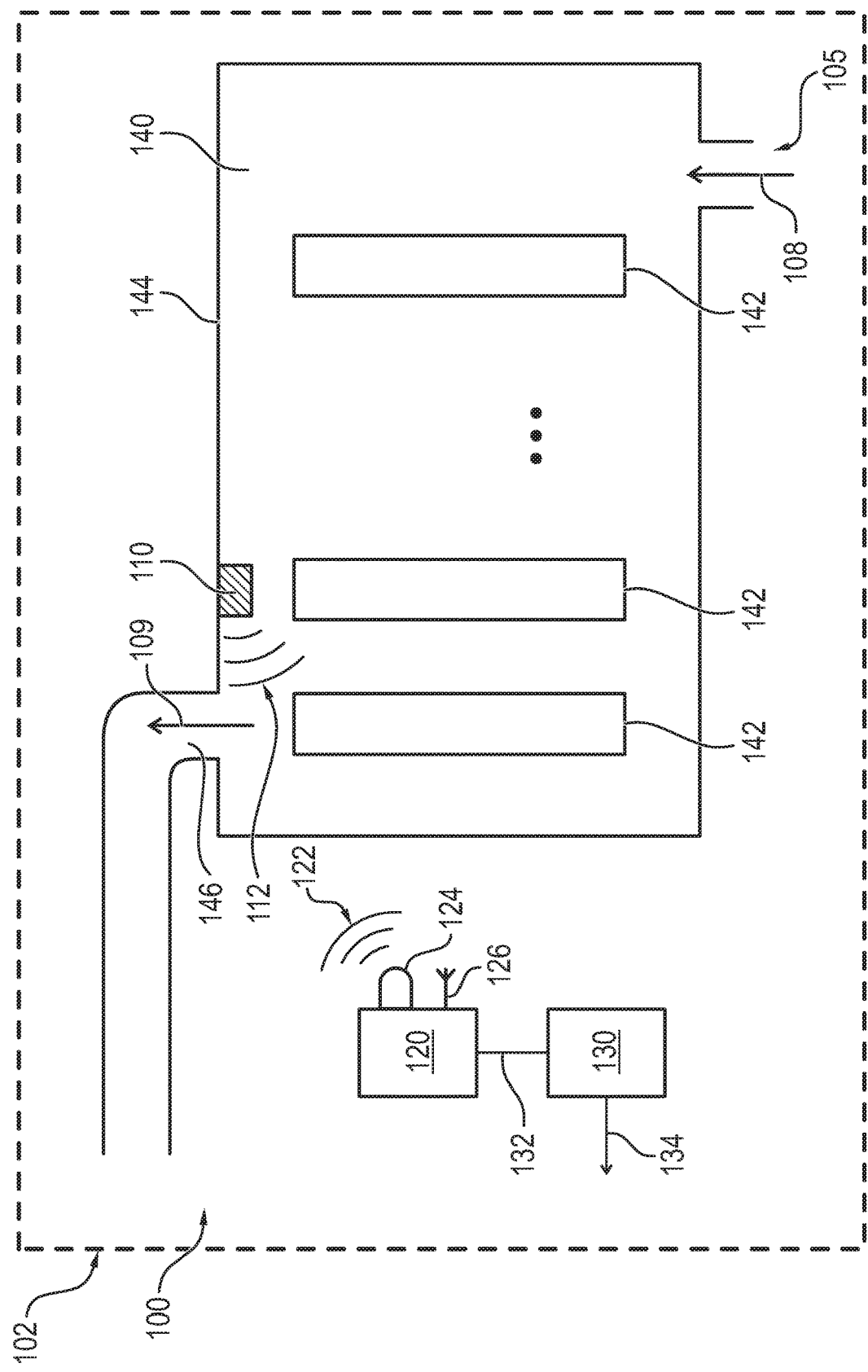
FIG. 1 is a schematic view of a first exemplary embodiment of a control system according to the present invention.

Referring to the drawings, FIG. 1 shows a schematic view of a first exemplary embodiment of a control system 100 according to the present invention.

The control system 100 is configured to control the temperature of a breathing gas circuit 105 in a closed-circuit respirator 102. The control system 100 comprises a temperature sensor unit 110, a temperature-reading unit 120 and a control unit 130. The closed-circuit respirator may comprise a housing surrounding the component space with several breathing components as disclosed in U.S. Patent Application Publication 2019/0184212, which is hereby incorporated by reference in its entirety.

The temperature sensor unit 110 is configured to send a temperature signal 112 in the presence of a corresponding temperature polling signal. The temperature signal 112 indicates the temperature currently present in an area surrounding the temperature sensor unit 110. In the exemplary embodiment shown, the temperature sensor unit 110 advantageously comprises a radio frequency identification (RFID) tag with a temperature sensor, namely a temperature sensor embodied with an RFID tag. The exact mode of operation of an RFID temperature sensor is known as discussed above and will not therefore be explained in more detail. Furthermore, the temperature sensor unit 110 is arranged in the closed-circuit respirator 102 such that the temperature present in the area surrounding the temperature sensor 110 indicates a breathing gas temperature in an area of the breathing gas circuit 105 in the closed-circuit respirator 102. The temperature sensor unit 110 is arranged in this case within a cooling device 140 of the closed-circuit respirator 102, which is configured to cool a breathing gas 108 of the breathing gas circuit 105. The cooling device 140 has in this case a number of heat exchanger plates 142 for this purpose, which are filled with a respective coolant. The temperature sensor unit 110 is arranged in this case on an inner side of a device housing 144 of the cooling device 140 in the area of a gas outlet 146 of the cooling device 140. As a result, the temperature sensor unit 110 determines the temperature that the inhaled gas 109 of a user of the closed-circuit respirator 102 has after the inhaled gas leaves the cooling device 140 and consequently preferably immediately before it leaves the closed-circuit respirator 102. In one exemplary embodiment, not shown, the temperature sensor is arranged at a heat exchanger plate or at a housing enclosing the coolant. In another exemplary embodiment, not shown, the temperature sensor is arranged on an outer side of the device housing of the cooling device.

The temperature-reading unit 120 is arranged in the closed-circuit respirator 102 at a spaced location from the breathing gas circuit 105 and from the temperature sensor unit 110. The temperature-reading unit 120 is signal connected especially advantageously in a wireless manner to the temperature sensor unit 110. The temperature-reading unit 120 is embodied by an RFID reading unit in this case. This is configured to trigger the temperature polling at the temperature sensor unit 110 by sending a polling signal 122. The polling signal 122 is sent in this case as a broad-band signal at predefined time intervals. Furthermore, the temperature-reading unit 120 is configured to receive and to transmit the temperature signal 112 provided by the temperature sensor unit 110. The sending of the polling signal 122 takes place via a transmitting device 124 of the temperature-reading unit 120. The reception of the temperature signal 112 takes place via an antenna array 126 of the temperature-reading unit 120. The polling signal 122 is formed by a provided electromagnetic field, as it is known for a communication by means of RFID technology. The temperature sensor unit 110 is configured to modulate the electromagnetic field in a temperature-dependent manner and to bring about thereby the sending of the temperature signal 112. The temperature-reading unit 120 is configured in this case to detect such a modulation and to receive as a result the temperature signal 112 by means of an antenna array 126.

The control unit 130 is likewise arranged in the closed-circuit respirator 102 at a spaced location from the breathing gas circuit 105 and from the temperature sensor unit 110 and is signal connected to the temperature-reading unit 120. The control unit 130 comprises one or more processor and associated memory. This signal connection 132 takes place in a wired manner in this case. In one exemplary embodiment, not shown, the signal connection is embodied as a wireless connection, for example, via a radio connection. Furthermore, the control unit 130 is configured to determine the temperature indicated by the temperature signal 112 in the area surrounding the temperature sensor unit 110 and to output a control signal 134 as a function of this temperature. The control signal 134 is configured in this case to trigger an optical or acoustic control output at a user interface of the closed-circuit respirator 102.

Furthermore, the control unit 130 is configured in the exemplary embodiment shown to determine a coolant state of the cooling device 140 on the basis of the determined temperature, wherein the coolant state indicates an expected further cooling time of the cooling device 140. The control signal 134 is based in this case on the determined coolant state. The coolant state advantageously indicates an existing state of aggregation of the coolant within the cooling device 140.

The breathing gas circuit 105 is shown in FIG. 1 only in the area of the cooling device 140. As is known, it also comprises for the closed-circuit respirator 102 other areas, such as an area at a breathing bag and at a compressed gas cylinder, as well as at a $CO_2$ absorber of the closed-circuit respirator 102. Since the basic structure of a closed-circuit respirator 102 is known, it will not be discussed in detail below.

Figure 2:
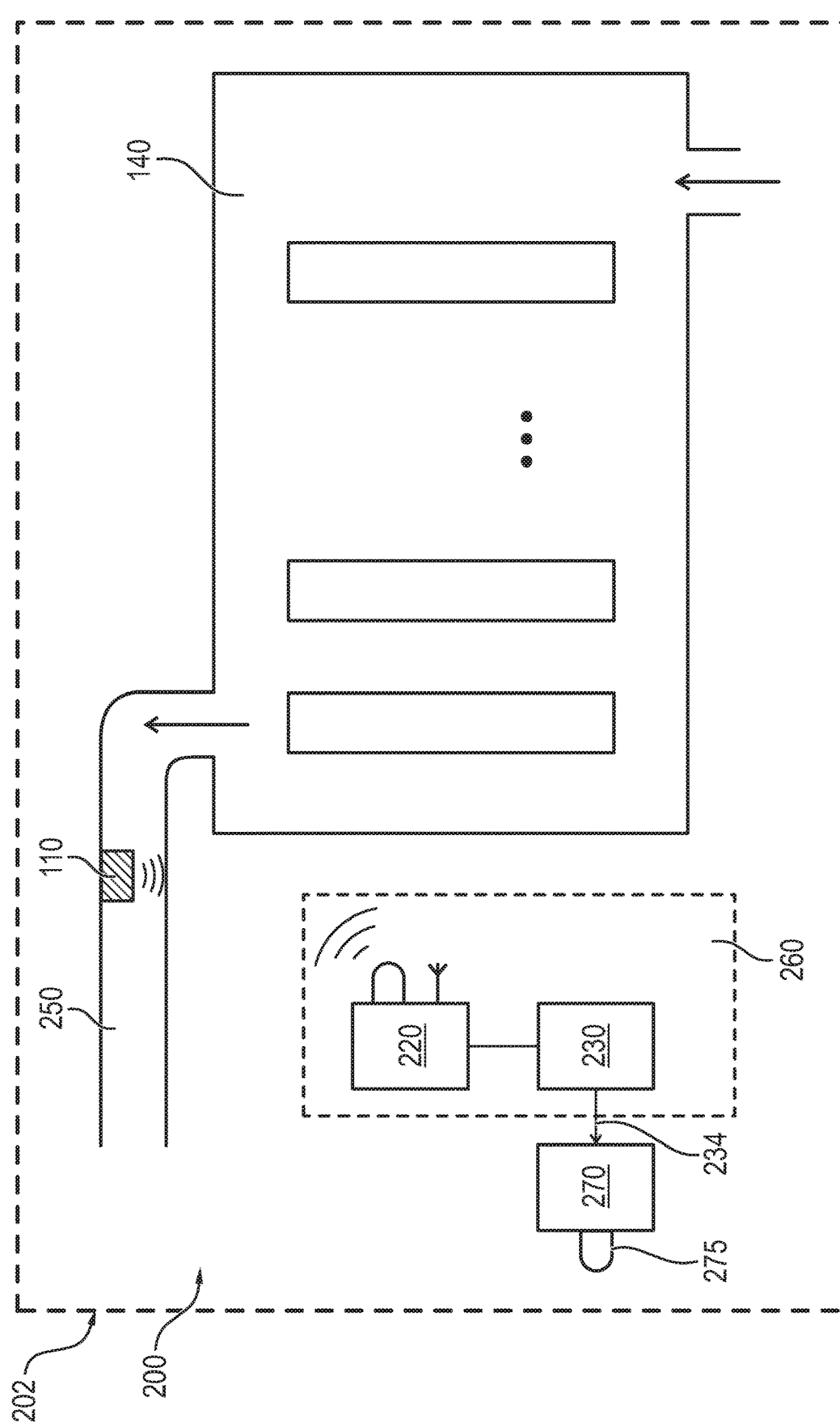
FIG. 2 is a schematic view of a second exemplary embodiment of the control system according to the present invention.

FIG. 2 shows a schematic view of a second exemplary embodiment of the control system 200 according to the present invention.

The control system 200 differs from the control system 100 shown in FIG. 1 in that the temperature sensor unit 110 is arranged in a supply line (closed-circuit respirator user connection line) 250, which is located between the cooling device 140 and a user of the closed-circuit respirator 202. As a result, the temperature of the inhaled gas can advantageously be determined directly in front of the user of the closed-circuit respirator 202. This makes it possible to check especially accurately whether the inhaled gas provided for the user exceeds a predefined temperature limit value. Furthermore, the arrangement of the temperature sensor unit 110 in the supply line 250 reduces the risk of inaccuracies developing in the temperature determined on the basis of the temperature inhomogeneities within the cooling device 140.

Further, the control unit 230 of the control system 200 includes processor and memory features as noted but differs from the control unit 130 from FIG. 1 in that the control unit 130 is arranged, together with the temperature-reading unit 220, within a control system housing/area 260 of the closed-circuit respirator 202. As a result, a majority of the electronic components of the closed-circuit respirator 202 are advantageously accommodated within a single area, which can advantageously be protected, for example, by a housing, from the other components and from a corresponding thermal stress within the closed-circuit respirator 202.

Another difference between the exemplary embodiments shown in FIG. 1 and FIG. 2 is that the control signal 234 is outputted directly to a user interface 270 in a wired manner. Due to an optical output medium 275, the user interface 270 provides an optical output, which outputs an optical warning signal as a control output in case the determined temperature exceeds a predefined temperature limit value.

Figure 3:
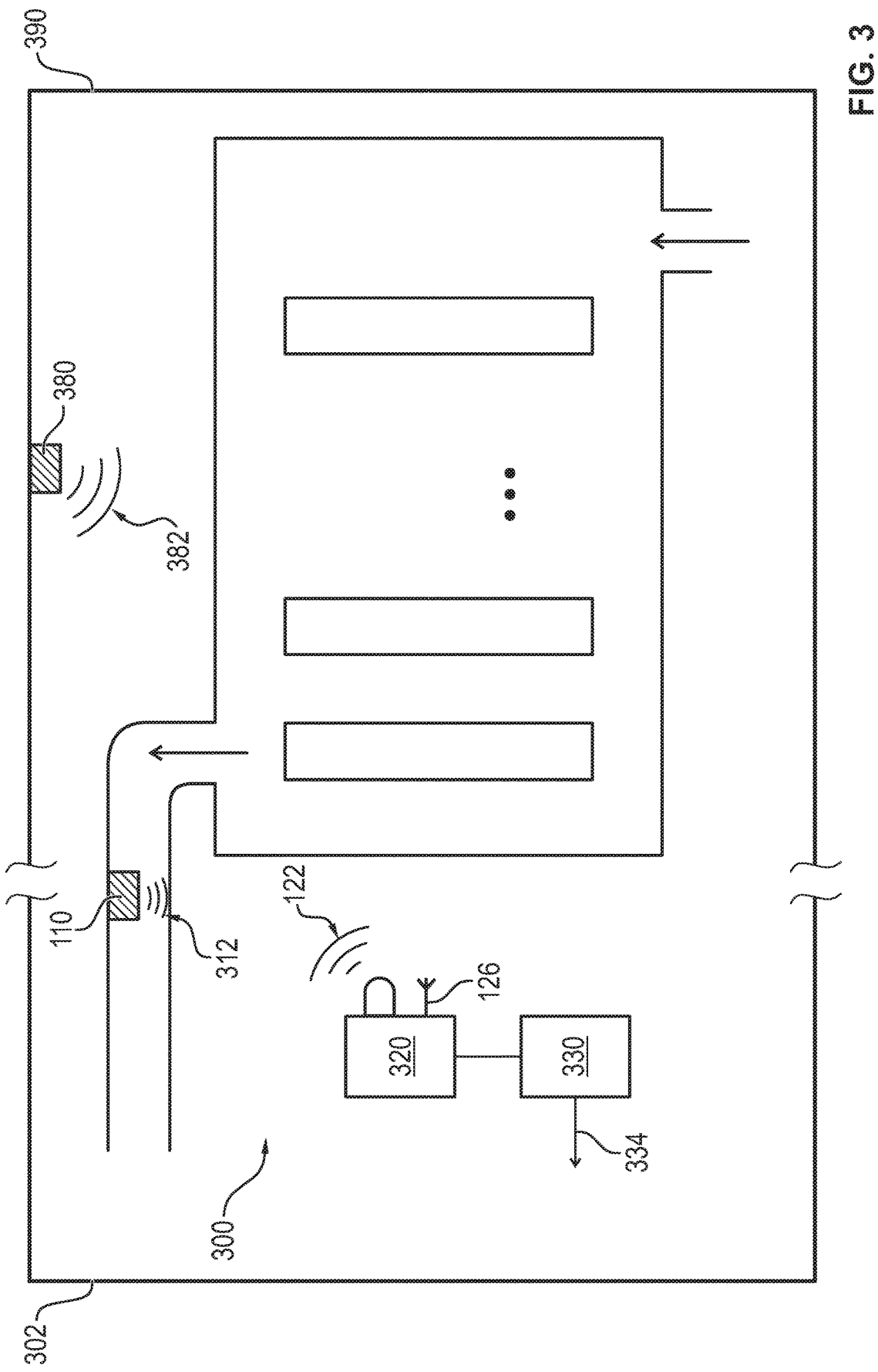
FIG. 3 is a schematic view of a third exemplary embodiment of the control system according to the present invention.

FIG. 3 shows a schematic view of a third exemplary embodiment of the control system 300 according to the present invention.

The control system 300 corresponds to the control system 200 shown in FIG. 2, with the difference that it has an additional comparison temperature sensor unit 380.

In this case, the additional comparison temperature sensor unit 380 is a comparison temperature sensor 380, which is embodied by means of an RFID tag. The comparison temperature sensor 380 is configured to send a comparison temperature signal 382 in the presence of a corresponding comparison temperature polling. The comparison temperature signal 382 indicates the comparison temperature currently present in an area surrounding the comparison temperature sensor unit 380. The comparison temperature polling is triggered by the comparison temperature polling signal, which is the same polling signal 122 in this case as the signal that also triggers the temperature signal 312 of the temperature sensor unit 110. As a result, values that were determined at approximately the same time by the respective temperature sensor unit 110, 380 are available for the temperature and for the comparison temperature. In an alternative embodiment, the temperature-reading unit sends a comparison polling signal that is separate from the polling signal.

The temperature-reading unit 320 is further configured to receive the comparison temperature signal 382 sent by the comparison temperature sensor unit 380. The control unit 330 is further configured to determine the comparison temperature indicated by the comparison temperature signal 382 and to output the control signal 334 as a function of the temperature and the comparison temperature. The control signal depends in this case on a temperature difference between the comparison temperature and the temperature.

The comparison temperature sensor unit 380 is arranged on an inner side of a housing 390 of the closed-circuit respirator 302. The temperature difference consequently indicates a temperature difference between an inner temperature of the closed-circuit respirator 302 and the temperature of the inhaled gas provided for the user. In one exemplary embodiment, not shown, the comparison temperature sensor is arranged in the area of the $CO_2$ absorber or in the areas of the breathing bag of the closed-circuit respirator. Consequently, an effective output of the cooling device provided can be estimated in this exemplary embodiment by the determined temperature difference. In another exemplary embodiment, not shown, the comparison temperature sensor is arranged on an outer side of the housing of the closed-circuit respirator.

The comparison temperature signal 382 also comprises, in addition to the indication of the measured comparison temperature, the indication of comparison identification information. The temperature signal 312 also comprises, in addition to the measured temperature, the indication of identification information. The identification information and the comparison identification information make possible an unambiguous assignment between the indicated temperature and the respective temperature sensor unit 110, 380 providing the temperature. This is especially advantageous for the exemplary embodiment shown, because both the temperature signal 312 and the comparison temperature signal 382 can be received by a single antenna array 126 and assigned to the respective providing temperature sensor on the basis of the corresponding identification information.

In one exemplary embodiment, not shown, the control system has at least one additional comparison temperature sensor. As a result, the temperature can advantageously be checked in different areas of the closed-circuit respirator and preferably compared with predefined temperature limit values.

Figure 4:
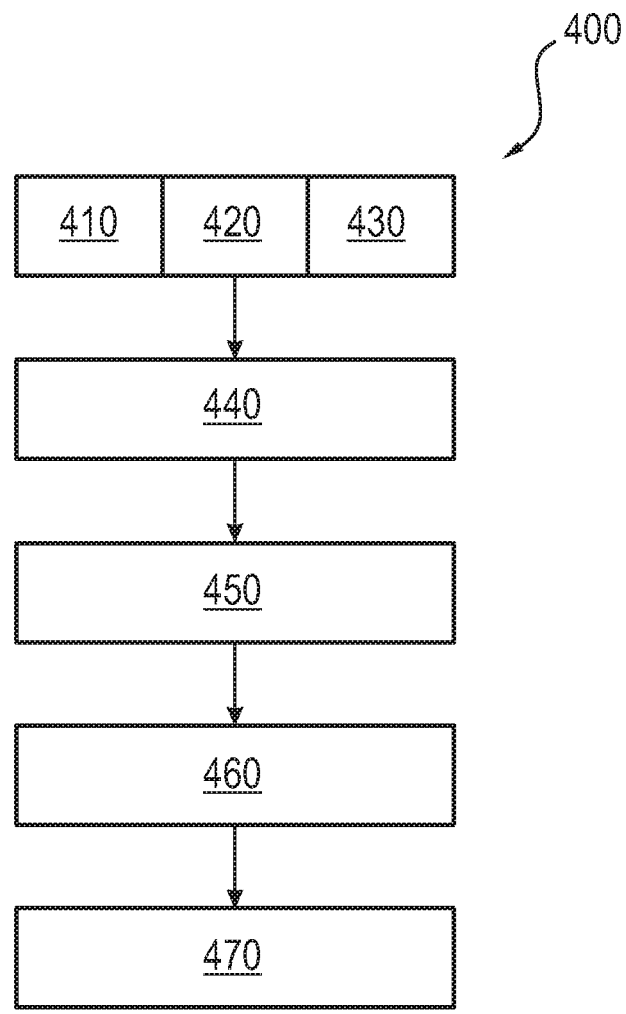
FIG. 4 is a flow chart of a first exemplary embodiment of a process according to the present invention.

FIG. 4 shows a flow chart of a first exemplary embodiment of a process 400 according to the present invention.

The process 400 for controlling a breathing gas circuit in a closed-circuit respirator has the steps indicated below.

A first step 410 comprises the provision of a temperature sensor unit, especially of a temperature sensor embodied by means of an RFID tag, such that a temperature present in an area surrounding the temperature sensor indicates a breathing gas temperature in an area of the breathing gas circuit in the closed-circuit respirator.

Another step 420 comprises the arrangement of a temperature-reading unit, especially a temperature-reading unit embodied by means of an RFID reading unit, at a spaced location from the breathing gas circuit and from the temperature sensor unit.

A next step 430 comprises the provision of a control unit, at a spaced location from the breathing gas circuit and from the temperature sensor unit, and a connection of the control unit to the temperature-reading unit for signal technology.

The steps 410, 420 and 430 may be carried out independently from one another during the manufacture or maintenance of the closed-circuit respirator.

Another step 440 comprises the sending of a polling signal to trigger a temperature polling by the temperature-reading unit to the temperature sensor unit.

A next step 450 of the process 400 comprises the sending of a temperature signal in the presence of the corresponding temperature polling by the temperature sensor unit, the temperature signal indicating the temperature currently present in the area surrounding the temperature sensor.

A next step 460 comprises the reception of the temperature signal sent by the temperature sensor.

A final step 470 comprises the determination of the temperature indicated by the signal in the area surrounding the temperature sensor, and the outputting of a control signal as a function of this temperature.

The steps 440, 450, 460 and 470 are repeated corresponding to predefined time intervals, at which the temperature-reading unit triggers the temperature polling at the temperature sensor.

The outputting of the control signal according to step 470 preferably comprises a prior determination of a coolant state of the cooling device of the closed-circuit respirator on the basis of the determined temperature. The coolant states indicates an expected further cooling time of the cooling device. A future rise of the temperature of the inhaled gas is advantageously checked thereby. The determined coolant state preferably indicates a state of aggregation of the coolant of the cooling device.

Figure 5:
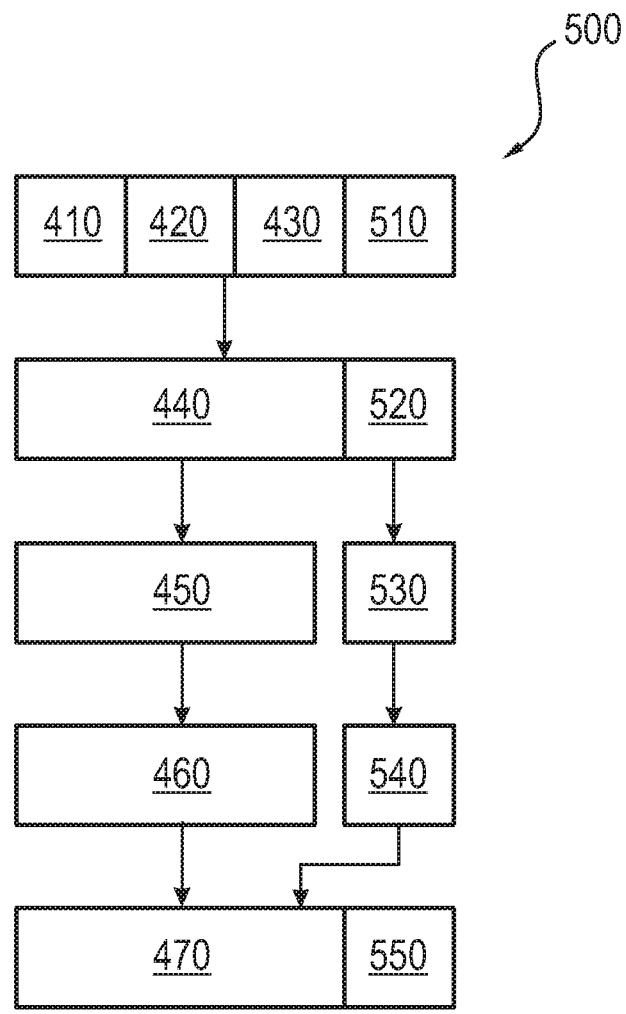
FIG. 5 is a flow chart of a second exemplary embodiment of the process according to the present invention.

FIG. 5 shows a flow chart of a second exemplary embodiment of the process 500 according to the present invention.

The process 500 comprises all the steps shown in FIG. 4 and has, furthermore, the steps described below.

A first step 510 comprises the provision of at least one comparison temperature sensor unit, especially of a comparison temperature sensor unit embodied by an RFID tag including a temperature sensor, in the closed-circuit respirator.

Just like the steps 410, 420 and 430, step 510 may be carried out before a use of the closed-circuit respirator, especially during the manufacture or maintenance of the closed-circuit respirator.

A next step 520 comprises the sending of a comparison polling signal by the temperature-reading unit to trigger a comparison temperature polling at the at least one comparison temperature sensor unit.

A further step 530 comprises the sending of a comparison temperature signal in the presence of the corresponding comparison temperature polling, the comparison temperature signal indicating the temperature currently present in the area surrounding the at least one comparison temperature sensor unit.

A next step 540 of the process 500 comprises the reception of the comparison temperature signal sent by the comparison temperature sensor unit.

A next step 550 comprises the determination of the comparison temperature indicated by the comparison temperature signal and the outputting of the control signal as a function of the temperature and the comparison temperature.

As is shown in FIG. 5, step 520 typically takes place approximately simultaneously with step 450, and step 540 takes typically place approximately simultaneously with step 460. Step 550 typically complements step 470. As was already explained in connection with FIG. 4, these steps are preferably carried out at predefined time intervals, which are predefined in time by the regular sending of the polling signal and of the comparison polling signal.

In this case, the comparison polling signal and the polling signal are the same signal that was discussed in connection with FIG. 3.

The outputting of the control signal according to step 550 takes place as a function of a temperature difference between the comparison temperature and the temperature. As a result, an effectively occurring cooling of the cooling device can especially advantageously be estimated. This makes it preferably possible to estimate an expected further cooling time of the cooling device of the closed-circuit respirator according to the present invention on the basis of empirical data.

While specific embodiments of the invention have been shown and described in detail to illustrate the application of the principles of the invention, it will be understood that the invention may be embodied otherwise without departing from such principles.

LIST OF REFERENCE NUMBERS

100, 200, 300 Control system
102, 202, 302 Closed-circuit respirator
105 Breathing gas circuit
108 Breathing gas 109 Inhaled gas
110 Temperature sensor unit
112, 312 Temperature signal
120, 220, 320 Temperature-reading unit
122 Polling signal, comparison polling signal
124 Transmission device
126 Antenna array
130, 230, 330 Control unit
132 Connection
134, 234, 334 Control signal
140 Cooling device
142 Heat exchanger plate
144 Device housing
146 Gas outlet
250 Supply line
260 Control system
270 User interface
275 Output medium
380 Comparison temperature sensor unit
382 Comparison temperature signal
390 Housing of the closed-circuit respirator
400, 500 Process
410, 420, 430, 440, 450, Process steps
460, 470, 510, 520, 530,
540, 550

What is claimed is:

1. A control system for controlling a breathing gas circuit in a closed-circuit respirator, the control system comprising:
a temperature sensor unit comprising a temperature sensor and a radio frequency identification (RFID) tag, the temperature sensor unit being configured to send a temperature signal in a presence of a corresponding temperature polling signal, wherein the temperature signal indicates a temperature currently present in an area surrounding the temperature sensor, wherein the temperature sensor unit is arranged in an area adjacent to a breathing gas outlet of a cooling device housing of the closed-circuit respirator or in a supply line between the cooling device and a user of the closed-circuit respirator such that the temperature present in the area surrounding the temperature sensor indicates a breathing gas temperature in an area of the breathing gas circuit in the closed-circuit respirator;
a temperature-reading unit comprising an RFID reading unit connected with the closed-circuit respirator and disposed at a spaced location from the breathing gas circuit and from the temperature sensor unit, the RFID reading unit being configured to trigger the temperature polling at the temperature sensor unit by sending the temperature polling signal, and being configured to receive the temperature signal sent by the temperature sensor unit; and
a control unit connected with the closed-circuit respirator and disposed at a spaced location from the breathing gas circuit and from the temperature sensor unit, the control unit being signal connected to the temperature-reading unit and being configured to determine the temperature indicated by the temperature signal and to output a control signal as a function of the indicated temperature, the control unit being further configured to determine a coolant state of the cooling device on the basis of the determined temperature, wherein the coolant state indicates an expected further cooling time of the cooling device.

2. A control system in accordance with claim 1, wherein the RFID tag comprises a passive RFID tag.

3. A control system in accordance with claim 1, wherein the temperature sensor is arranged in the supply line connected to the closed-circuit respirator, the supply line comprising a supply line end area, the supply line end area being adjacent to the breathing gas outlet of the cooling housing of the closed-circuit respirator.

4. A control system in accordance with claim 1, wherein the temperature sensor is arranged in an interior space of the cooling device housing of the closed-circuit respirator or an end area of the supply line located adjacent to the breathing gas outlet.

5. A control system in accordance with claim 1, wherein the control unit is configured:
to output the control signal based on the determined coolant state.

6. A control system in accordance with claim 1, further comprising at least one comparison temperature sensor unit comprising a comparison temperature sensor and an RFID tag, wherein:
the at least one comparison temperature sensor unit is configured to send a comparison temperature signal in a presence of a corresponding comparison temperature polling signal;
the comparison temperature signal indicates the comparison temperature present in an area surrounding the at least one comparison temperature sensor unit;
the temperature-reading unit is further configured to trigger the comparison temperature polling at the at least one comparison temperature sensor unit by sending the comparison polling signal and to receive the comparison temperature signal sent by the at least comparison temperature sensor unit; and
the control unit is further configured to determine the comparison temperature indicated by the comparison temperature signal and to output the control signal as a function of the temperature and the comparison temperature.

7. A control system in accordance with claim 6, wherein the control unit is configured to output the control signal as a function of a temperature difference between the comparison temperature and the temperature.

8. A control system in accordance with claim 6, wherein the at least one comparison temperature sensor unit is arranged in a supply line between the cooling device and the user of the closed-circuit respirator, in a breathing bag of the closed-circuit respirator, at a closed-circuit respirator housing of the closed-circuit respirator or at a $CO_2$ absorber unit of the closed-circuit respirator.

9. A closed-circuit respirator comprising:
a breathing gas circuit;
a cooling device flow connected to the breathing circuit, the cooling device comprising a cooling device housing, the cooling device housing comprising a breathing gas outlet; and
a control system comprising:
a temperature sensor unit comprising a temperature sensor and a radio frequency identification (RFID) tag, the temperature sensor being arranged in an area adjacent to the breathing gas outlet of the cooling device housing or the temperature sensor being arranged in a supply line between the cooling device and a user of the closed-circuit respirator, the temperature sensor unit being configured to send a temperature signal in a presence of a corresponding temperature polling signal, wherein the temperature signal indicates a temperature currently present in an area surrounding the temperature sensor, wherein the temperature sensor unit is arranged at or adjacent to cooling device and/or the breathing gas circuit such that the temperature present in the area surrounding the temperature sensor indicates a breathing gas temperature of breathing gas in the closed-circuit respirator;

a temperature-reading unit comprising an RFID reading unit disposed at a spaced location from the breathing gas circuit and from the temperature sensor unit, the RFID reading unit being configured to trigger the temperature polling at the temperature sensor by sending the temperature polling signal, and being configured to receive the temperature signal sent by the temperature sensor unit; and a control unit connected disposed at a spaced location from the breathing gas circuit and from the temperature sensor unit, the control unit being signal connected to the temperature-reading unit and being configured to determine the temperature indicated by the temperature signal and to output a control signal as a function of the indicated temperature, the control unit being further configured to determine a coolant state of the cooling device on the basis of the determined temperature, wherein the coolant state indicates an expected further cooling time of the cooling device.

10. A closed-circuit respirator in accordance with claim 9, wherein the RFID tag comprises a passive RFID tag.

11. A closed-circuit respirator in accordance with claim 9, wherein the temperature sensor is arranged in the breathing gas circuit.

12. A closed-circuit respirator in accordance with claim 9, wherein the temperature sensor is arranged in an interior space of the cooling device housing or in an end area of the supply line located adjacent to the breathing gas outlet.

13. A closed-circuit respirator in accordance with claim 9, wherein the control unit is configured:
to output the control signal based on the determined coolant state.

14. A closed-circuit respirator in accordance with claim 9, further comprising at least one comparison temperature sensor unit comprising a comparison temperature sensor and an RFID tag, wherein:
the at least one comparison temperature sensor unit is configured to send a comparison temperature signal in a presence of a corresponding comparison temperature polling signal;
the comparison temperature signal indicates the comparison temperature present in an area surrounding the at least one comparison temperature sensor unit;
the temperature-reading unit is further configured to trigger the comparison temperature polling at the at least one comparison temperature sensor unit by sending the comparison polling signal and to receive the comparison temperature signal sent by the at least one comparison temperature sensor unit; and
the control unit is further configured to determine the comparison temperature indicated by the comparison temperature signal and to output the control signal as a function of the temperature and the comparison temperature.

15. A closed-circuit respirator in accordance with claim 14, wherein the control unit is configured to output the control signal as a function of a temperature difference between the comparison temperature and the temperature.

16. A closed-circuit respirator in accordance with claim 14, further comprising:

a supply line between the cooling device and a closed-circuit respirator user connection;
a breathing bag;
a housing of the closed-circuit respirator; and
a $CO_2$ absorber unit, wherein the at least one comparison temperature sensor is arranged in the supply line between the cooling device and the user of the closed-circuit respirator or in the breathing bag, or at a housing, or at the $CO_2$ absorber unit.

17. A process for controlling a breathing gas circuit in a closed-circuit respirator, the process comprising the steps of:
providing a temperature sensor unit comprising a temperature sensor and a radio frequency identification (RFID) tag, such that a temperature present in an area surrounding the temperature sensor indicates a temperature present in an area surrounding the temperature sensor in an area of the breathing gas circuit in the closed-circuit respirator, the temperature sensor being arranged in an area adjacent to a breathing gas outlet of a cooling device housing of a cooling device of the closed-circuit respirator or in a supply line between the cooling device and a user of the closed-circuit respirator;
arranging a temperature-reading unit comprising an RFID reading unit disposed at a spaced location from the breathing gas circuit and from the temperature sensor unit;
providing a control unit, at a spaced location from the breathing gas circuit and from the temperature sensor unit, and signal connecting the control unit to the temperature-reading unit;
sending a polling signal to trigger a temperature polling by the temperature-reading unit to the temperature sensor unit;
sending a temperature signal in the presence of the corresponding temperature polling by the temperature sensor unit, wherein the temperature signal indicates the temperature currently present in an area surrounding the temperature sensor;
receiving the temperature signal sent by the temperature sensor unit; and
determining the temperature indicated by the temperature signal in the area surrounding the temperature sensor and outputting a control signal as a function of the indicated temperature, wherein the outputting of the control signal by the control unit comprises the step of determining a coolant state of a cooling device of the closed-circuit respirator based on the determined temperature, wherein the coolant state indicates an expected further cooling time of the cooling device.

18. A process in accordance with claim 17, wherein the outputting of the control signal by the control unit comprises the step of:
outputting the control signal based on the coolant state.

19. A process in accordance with claim 18, further comprising the steps of:
providing at least one comparison temperature sensor unit, comprising a comparison temperature sensor and an RFID tag, in the closed-circuit respirator;
sending a comparison polling signal by the temperature-reading unit to trigger a comparison temperature polling at the at least one comparison temperature sensor unit;
sending a comparison temperature signal in the presence of the corresponding comparison temperature polling, wherein the comparison temperature signal indicates the comparison temperature currently present in an area surrounding the at least one comparison temperature sensor unit;

receiving the comparison temperature signal sent by the at least one comparison temperature sensor unit; and determining the comparison temperature indicated by the comparison temperature signal and outputting the control signal as a function of the temperature and the comparison temperature.

20. A process in accordance with claim 17, wherein the outputting of the control signal is carried out as a function of a temperature difference between a comparison temperature and the temperature.

* * * * *